United States Patent [19]

Merrick et al.

[11] Patent Number: 5,357,953
[45] Date of Patent: Oct. 25, 1994

[54] MEASUREMENT DEVICE AND METHOD OF CALIBRATION

[75] Inventors: Edwin B. Merrick, Stow; Amal Jeryes, Tewksbury; Neal B. Dowling, Jr., Sudbury, all of Mass.; Yuan Young, Encinitas; Larry Powell, Carlsbad, both of Calif.

[73] Assignee: Puritan-Bennett Corporation, Carlsbad, Calif.

[21] Appl. No.: 886,636

[22] Filed: May 21, 1992

[51] Int. Cl.$^5$ .............................................. A61B 5/00
[52] U.S. Cl. ..................................... 128/633; 128/664; 128/665; 356/39
[58] Field of Search .................... 128/633–634, 128/664–665, 666–667; 356/39–41

[56] References Cited

U.S. PATENT DOCUMENTS

| | | | |
|---|---|---|---|
| 3,900,396 | 8/1975 | Lamadrid | 210/94 |
| 4,237,900 | 12/1980 | Schulman et al. | 128/630 |
| 4,243,531 | 1/1981 | Crockett et al. | 210/188 |
| 4,253,156 | 2/1981 | Lisle et al. | 364/571 |
| 4,418,392 | 11/1983 | Hata | 364/571 |
| 4,446,715 | 5/1984 | Bailey | 128/634 X |
| 4,558,416 | 12/1985 | Pauwels et al. | 364/431 |
| 4,621,643 | 11/1986 | New, Jr. et al. | 128/633 |
| 4,651,741 | 3/1987 | Passafaro | 128/633 |
| 4,691,173 | 9/1987 | Mollett et al. | 330/144 |
| 4,707,683 | 11/1987 | Yao | 340/347 |
| 4,748,598 | 5/1988 | Kopke | 367/13 |
| 4,854,321 | 8/1989 | Boiarski | 128/634 |
| 4,898,333 | 2/1990 | Kime et al. | 239/657 |
| 4,931,803 | 6/1990 | Shimko | 342/371 |
| 4,942,877 | 7/1990 | Sakai et al. | 128/633 |
| 4,993,419 | 2/1991 | Pompei et al. | 128/664 |
| 5,058,588 | 10/1991 | Kaestle | 128/633 |

OTHER PUBLICATIONS

Datakey, Serial Memory Keys, Models DK1000, DK2000 & DK4000.
Datakey, Model KC4210 Keyceptacle Access Device for the 1K, 2K & 4K Serial Data Keys.
Data key, Model KT4210 Keytroller Interface Controller for the 1K, 2K & 4K Serial Data Keys.

*Primary Examiner*—Angela D. Sykes
*Attorney, Agent, or Firm*—Fulwider Patton Lee & Utecht

[57] ABSTRACT

A calibration method and apparatus capable of being calibrated according to the method that allows a remote sensor to be transferred from analyzing instrument to analyzing instrument within a group of analyzing instruments without the need to recalibrate. The device includes a separate memory capability associated with the sensor as well as each instrument while the method requires the use of an arbitrarily selected sensor to initially be transferred from instrument to instrument, while being subjected to the same calibration standards in order to generate calibration data for entry into each instrument's memory. With such data entered in the instruments' memories, any remote sensor, calibrated on any one instrument and having such calibration data stored in its own memory, can then readily be interconnected to any instrument of the group to immediately yield accurate results.

30 Claims, 5 Drawing Sheets

MEASUREMENT DEVICE AND METHOD OF CALIBRATION

BACKGROUND OF THE INVENTION

The present invention relates generally to the calibration of measurement devices and more particularly pertains to the calibration of measurement systems wherein remote sensors optically interact with analytical instruments.

Measuring devices often comprise multicomponent systems wherein a remote sensor or probe component generates a signal in response to a certain condition and a processing or analyzing instrument is employed to convert such signal into meaningful data. Both the sensor component as well as the processing component are typically subject to variation in that the actual signal generated by a sensor in response to a given condition may vary from sensor to sensor and the output generated by the instrument in response to a given signal as received from a sensor may vary from instrument to instrument. It is therefore necessary to calibrate the sensor component, the instrument component or both such that accurate results are obtained in response to given conditions. Calibration efforts are considerably more complex in systems wherein any of a plurality of probes are intended to interact with any of a plurality of instruments. Calibration efforts are further complicated in systems wherein the raw signal generated by the probe is at least partially dependant upon instrument input. Additional problems are inherent in systems wherein electronic and optical componentry is combined.

Certain invasive optical blood gas analyzers are examples of measurement systems subject to all of the above set forth complexities relating to calibration. Such systems present a selected fluorescing medium to blood flow, irradiate the medium to induce fluorescence and compare the excitation radiation's intensity with the intensity of the resulting fluorescence. The medium is selected such that its rate of fluorescence is quenched by the presence of a certain gas to render the resulting intensity ratio a function of the concentration of such gas. A probe employing the described medium, when introduced into a patient's vasculature, can therefore provide real time indications of the partial pressures of certain gasses within the patient's blood supply. Because such probes cannot be reused, the system must be designed to render their disposability economically feasible.

The type of invasive optical blood gas analyzing system especially difficult to calibrate is a system wherein the excitation signal is generated within the analyzing instrument, conducted to the probe via an optic fiber, and fluorescence, emitted by the probe, is returned to the instrument via the optic fiber for analysis. By retaining a substantial portion of the optical hardware within the instrument, the cost of the probe is substantially reduced but considerable calibration problems are introduced as a direct result of such a separation of the optics. Variations inherent in the probe include the sensitivity of the particular deposit of fluorescing medium employed therein and the transmission qualities of the optical conduit and optical coupler. Variations inherent in the instrument include the output of the radiation source, the sensitivities of the sensors measuring the outgoing and incoming radiation intensities as well as the transmission qualities of the optical conduits and couplers. Simply calibrating the probe will not compensate for variation in the instrument and vice versa. In order for the system to produce accurate results, all these sources of variation must be compensated for with respect to each individual instrument and probe combination.

While the calibration of each probe and instrument combination just prior to use would ensure accurate results, such calibration efforts are not always practical or even possible in the environment where and under the conditions which such blood gas analyzers are typically put to use. It is often desirable to be able to transfer a particular probe from one instrument to another without the need to recalibrate the new probe and instrument combination upon transfer. Such situations arise when transferring a patient from an operating room to a recovery area where the movement of the analytical instrument is impractical. It is most desirable to be able to leave the probe in position within the patient's vasculature, disconnect the probe from the instrument located in the operating room, transfer the patient into any of a number of recovery areas and immediately reconnect the probe to an instrument located there. Removing the first probe and inserting a new probe calibrated to the second instrument is contraindicated due to the increased probability of infection and the additional effort involved. A number of calibration techniques have heretofore been suggested in an effort to overcome this "transportability" problem inherent in this type of analytical equipment, but each suffers from substantial shortcomings as set forth in more detail below.

It has been suggested that upon arrival in the recovery area, a blood sample would be drawn for analysis and that the second instrument's output would then merely be adjusted to conform to the lab results. This however assumes that the second instrument's calibration is merely in need of an offset adjustment and ignores any slope changes that may in fact be necessary. Moreover, the patient's blood gasses may be subject to substantial fluctuation during the time elapsed between the time when the blood sample was drawn and the time when the instrument is actually recalibrated. Such errors would most likely occur in the case of an unstable patient while it is precisely the unstable patient that is most dependent upon accurate information.

An alternative approach has been proposed wherein a dual sensor probe component is used in conjunction with appropriately modified analyzing instrumentation. One of the sensors is intended for introduction into the patient's vasculature while the second sensor remains available for calibration at all times. This approach, however, requires the two sensors to be identically responsive to the presence of the gasses being tested for, which may introduce considerable if not insurmountable manufacturing problems. Moreover, such modification would add considerable cost to that component of the system which is intended to be disposed of after every use. Adaptation of the analyzing instrument to accommodate an additional sensor and to process information generated thereby would further add considerable cost to the system. Finally, although such approach allows a probe to remain within a patient and provide accurate information when interconnected to a succession of instruments, a skilled labor-intensive calibration effort is nonetheless required with each transfer.

Alternatively, it has been suggested to integrate the optical components of the instrument in a portable optics module that remains interconnected to the probe residing within the patient at all times. Upon transfer, the optics module is disengaged from the analyzing instrument and transported to the recovery area where it is simply plugged into the second instrument. Incorporation of such a feature would, however, add cost to the instrumentation, as this approach does require that extra equipment be transported with the patient and logistical problems are posed by the necessity of keeping track of numerous such modules throughout a typical medical facility.

Another alternative approach involves the use of a universal standard to which all of the instruments in use would be calibrated such that a given signal received from any probe would yield the same value on every instrument. Since instrument performance is subject to drift and degradation, calibration of the instruments would have to be performed on a periodic basis and cannot simply be permanently accomplished at the time of manufacture. Return of the instruments to a central facility for periodic recalibration would be an impracticable alternative, so this approach would require the development of calibration standards which could engage the instruments in the field. Such calibration standards would have to be sufficiently stable so as to be transportable all over the world, yet capable of exactly representing actual probes in all optical respects. The development and production of such a universal standard is a formidable undertaking. The necessity for acquiring and maintaining such standards would add cost to the system.

The prior art is devoid of a practical solution for maintaining a plurality of analyzing instruments of the type described in calibration. An approach is called for that allows a probe to be transferred from instrument to instrument without the need to undertake any recalibration efforts and that achieves such function without a substantial increase in cost and complexity.

SUMMARY OF THE INVENTION

The present invention provides for the calibration of measurement devices, such that a disposable sensor probe can be transferred from instrument to instrument without the need to recalibrate each successive probe and instrument combination. The approach does not add substantial cost to the disposable probe component nor to the analyzing instrument component, and requires relatively little effort to implement.

The present invention calls for each instrument to be provided with a non-volatile memory and computing capability and each sensor probe to be provided with a non-volatile memory accessible by any instrument to which the sensor is interconnected. No special calibration probes are needed and no complex calibration procedures are employed.

Any probe that would normally be utilized in conjunction with the instrumentation may be arbitrarily chosen to function as a transfer probe for calibrating all of the instruments in a particular group of instruments. Such group may for example include all of those instruments in a particular medical facility. In order to implement the calibration process of the present invention, the selected probe is interconnected to any arbitrarily chosen first instrument of the group of instruments and subjected to a first calibration standard. The calibration standard consists of a mixture of analytes, including analytes to which the probe is sensitive. The actual concentration values of analytes need not be known for the purposes of the instrument calibration routine.

During the calibration routine, the first instrument's output is stored in the transfer probe's memory, such output may or may not accurately reflect the actual value of the calibration standard's particular mixture of analytes. The probe is subjected to a second calibration standard containing a different mixture of the same analytes and the second output is stored in the transfer probe's memory. Two or more data points for each analyte will allow the instrument's computing ability to establish a separate calibration curve for each analyte defined in terms of slope and intercept. Additional data points enable the generation of more complex curves.

With the first instrument's output stored in its memory, the transfer probe is then transferred to a second instrument and again subjected to the same calibration standards. In this second and all subsequent instrument calibration routines, any corrections to the instrument's output that are necessary in order to bring such output into parity with the values stored in the probe's memory are entered in the instrument's memory. Each instrument with its individualized set of conversion factors stored therein will in effect emulate the response of the first instrument to probe input.

Once all instruments in the group have been calibrated in this manner, any probe can be calibrated on any instrument and then transferred to any other instrument without the need to perform a further recalibration. In order to calibrate a probe, the probe is interconnected to any one of the calibrated instruments of the group and subjected to at least two calibration standards of known values. Any corrections necessary to correct that instrument's output so as to conform to the known values of the standards are entered in the probe's memory. Each instrument's computing ability utilizes any correction factors stored in the probe's memory and any correction factors stored in its own memory to transform the generated raw signal into an accurate output.

Each instrument is transmitted the raw data from the sensor probe. The instrument's computing ability algorithmically corrects such raw data into corrected measurement values. The instrument corrects optical ratios according to the data stored in the instrument's memory and the data stored in the probe's memory is utilized to adjust algorithms which then produce an accurate representation of the conditions sensed by the probe. In order to compensate for any drift or degradation of any of the instruments' performance, the transfer calibration routine is repeated on a periodic basis.

Other features and advantages of the present invention will become apparent from the following detailed description, taken in conjunction with the accompanying drawings, which illustrate, by way of example, the principles of the invention.

DESCRIPTION OF THE PREFERRED EMBODIMENTS

The present invention as applied to an invasive optical blood gas analyzer facilitates the transfer of a patient from operating room to recovery area, in that a probe, positioned within the patient's vasculature, can remain in place and simply be disconnected from the analyzing instrument located in the operating room and reconnected to an analyzing instrument in the recovery area without the need for any recalibration to be performed.

Figure 1:
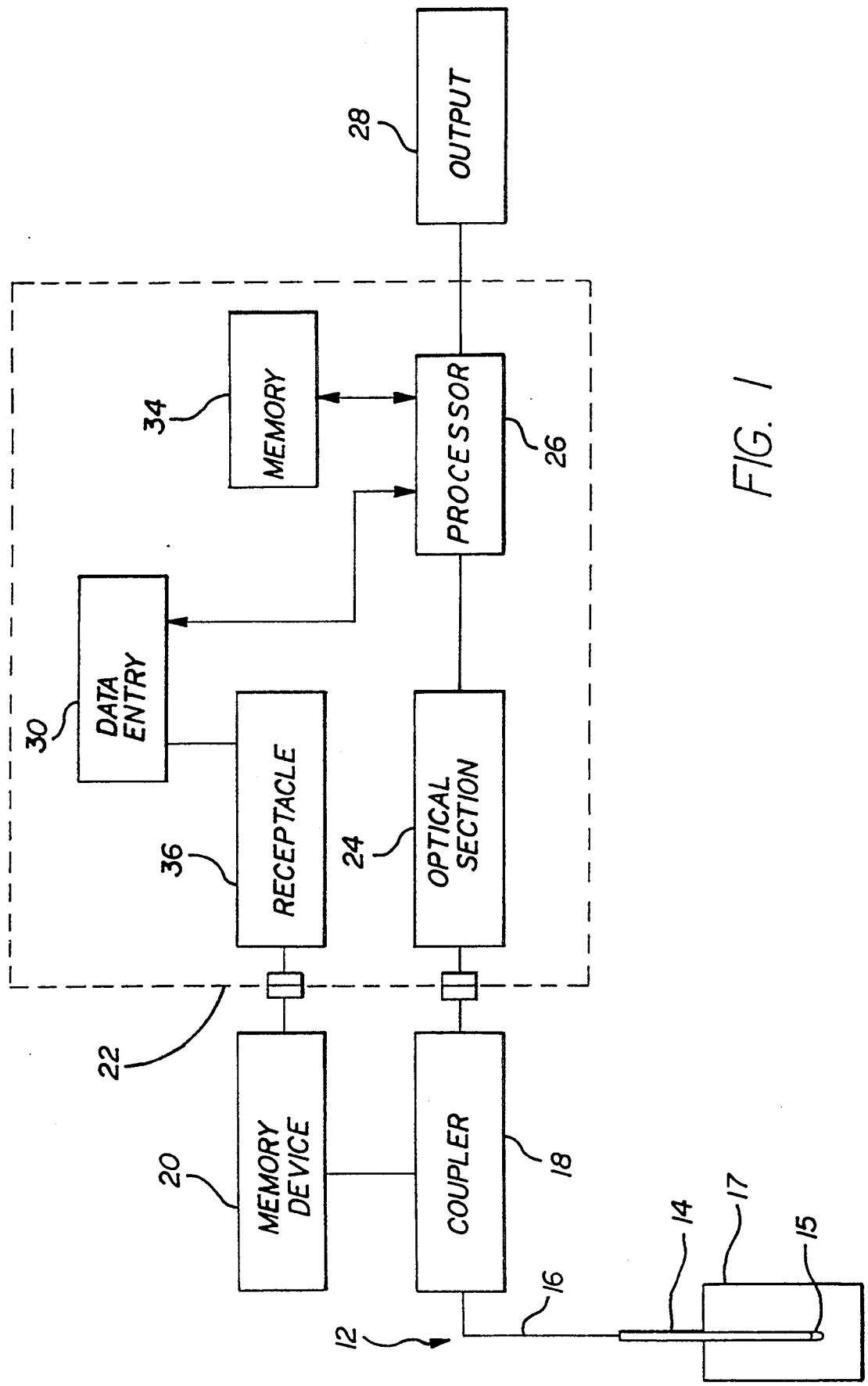
FIG. 1 is a schematic representation of a measurement system capable of calibration as per the method of the present invention.

FIG. 1 schematically illustrates an invasive optical blood gas analyzer of the type capable of benefiting from the method of the present invention. The measurement device consists of a two component system. The first component is a remote sensor component 12 which includes probe 14 which is insertable into the patient's vasculature. The second component is an analyzing instrument component 22 which generates an output 28 representative of the conditions to which probe 14 is subjected.

More particularly, probe 14 consists of a catheter carrying one or more optic fibers 16 therein having a deposit of one or more specially selected fluorescing media 15 near their tips. The media are selected to fluoresce in response to certain excitation signals supplied by instrument 22 while such fluorescence is subject to a quenching effect as a function of the presence of the gases of interest. By measuring the ratio of the excitation signal's intensity to the fluorescence intensity, the oxygen, carbon dioxide or pH level of a patient's blood supply can be determined. It is known that other blood components can be sensed by fluorescence. Therefore, the described apparatus could be applied to other blood components. Other blood parameters, such as temperature and pressure, may also be measured by the analyzing apparatus using well known analyzing instruments and sensors.

The probe's optic fiber 16 is interconnected to instrument 22 via coupler 18. A non-volatile memory device 20 is physically associated with sensor component 12 and can be interconnected to instrument 22. Data is entered into memory device 20 via data entry means 30 associated with instrument 22. Receptacle 36 allows for electrical connection between memory device 20 and the instrument's, 22, electronics, for example, data entry means 30 and processor 26. Data stored within memory 20 is accessible by the instrument's data processor 26. The instrument 22 includes an optical section 24 that serves to generate excitation signals, measure their intensities and conducts them to coupler 18. Additionally, the optical section 24 receives the fluorescence signal generated by sensor 12 through fibers 16 and measures their intensity.

A memory device 34 is contained within instrument 22 and is similarly accessible by processor 26. Data processor 26 receives intensity data from optical section 24, interprets it, and modifies it according to data stored in memory device 34 and memory device 20 and converts it into output 28. Each memory device is capable of storing the necessary correction factors or constants for each analyte. The electronic and optical hardware components necessary to perform these functions are well-known to those skilled in the art.

The remote sensor 12 is available as a relatively inexpensive single use item that is easily transportable with the patient while probe 14 remains in position within the patient's vasculature. Instrument 22 is a relatively large and expensive piece of equipment that is not ordinarily moved from room to room. Ideally, a medical facility would have a plurality of such instruments distributed throughout the facility as for example in various operating rooms and recovery rooms.

Figure 2A:
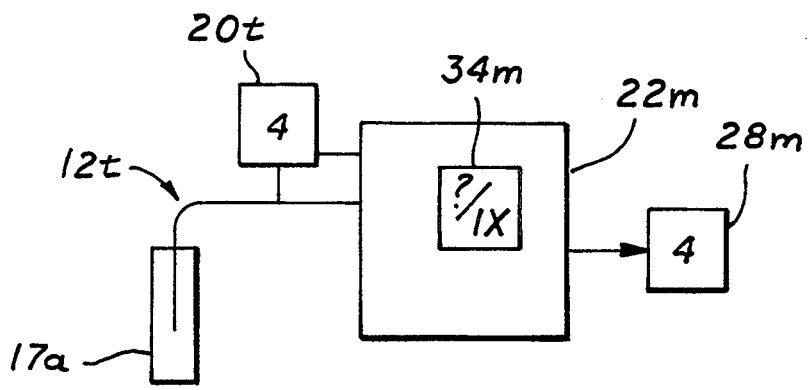
FIGS. 2a–d schematically illustrate the instrument calibration routine according to the method of the present invention.

The calibration method of the present invention first requires an instrument calibration routine to be performed on every instrument of a designated group of instruments. A probe is arbitrarily selected to function as a transfer probe, an instrument is arbitrarily selected to function as a master instrument. The transfer probe 12t is first interconnected to master instrument 22m as shown in FIG. 2a. Probe 12t is subjected to a calibration standard 17a which comprises a mixture of gasses that includes gasses to which the probe is sensitive. The partial pressures of these gasses need not be known for purposes of conducting the instrument calibration routine.

For purposes of simplification and illustration, the output of the combination of the selected transfer probe 12t, selected instrument 22m and calibration standard 17a yields an output 28m of a value of "4" which may or may not be an accurate representation of the partial pressure of the gas being tested within standard 17a. For example, the value of output 28m may represent the ratio of the optical intensities indicative of the fluorescence generated by the instrument and sensing components. In this initial step of the instrument calibration routine, this output value is entered directly into the probe's memory 20t via the data entry means. The master instrument's output 28m is a function of conversion factors stored in its own memory 34m, the precise value of which is in fact irrelevant and may be designated as 1x, or unity for purposes of simplification.

Figure 2B:
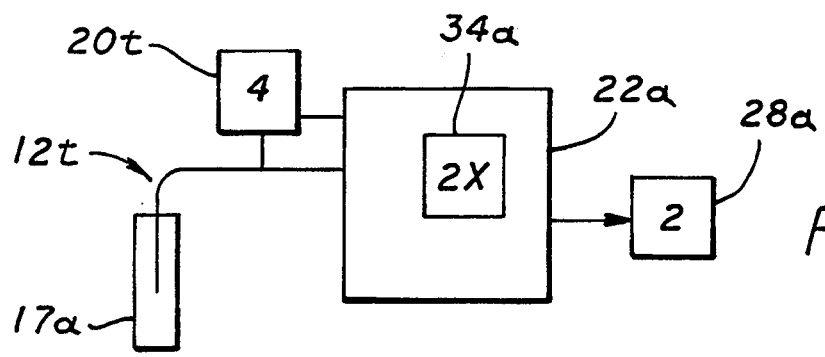

All outputs generated by this particular combination of instrument 22m and probe 12t with calibration standard 17a for the various analytes are stored in a similar manner in memory 20t. For purposes of simplification only, a single value from a single calibration standard is carried through FIGS. 2b, 2c and 2d.

Figure 2C:
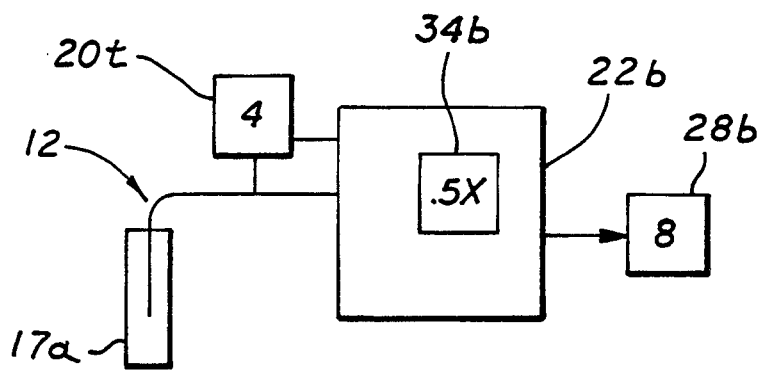
Figure 2D:
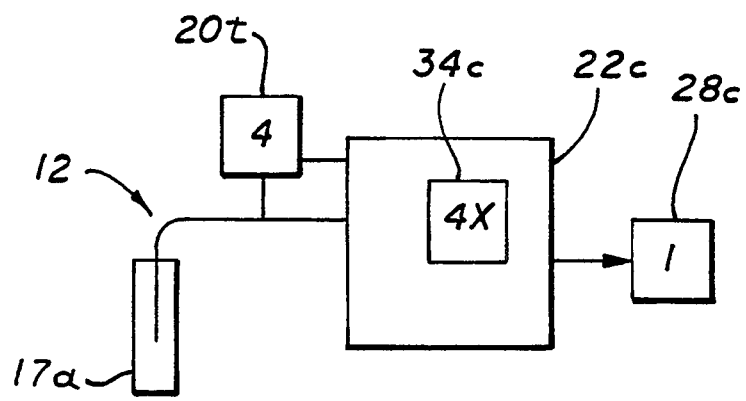

Once all of the values generated by master instrument 22m have been entered in the transfer probe's memory 20t, probe 12t is disconnected from instrument 22m and reconnected to instrument 22a. The transfer probe is again subjected to the same calibration standard 17a. Any corrections needed to bring the output from the new combination of this instrument 22a and probe 12t with calibration standard 17a into parity with the values stored in the probe's memory 20t are stored in the instrument's memory 34a. In the case illustrated in FIG. 2b, output 28a yields a value of "2" which would require its multiplication by a factor of 2× to conform to the "4" stored in probe memory 20t and hence a "2×" is entered into instrument memory 34a. A similar procedure is performed on each instrument in the group as illustrated in FIGS. 2c and 2d. This instrument calibration routine is periodically repeated in order to correct for any drift or degradation to which the instruments may be susceptible.

Figure 3A:
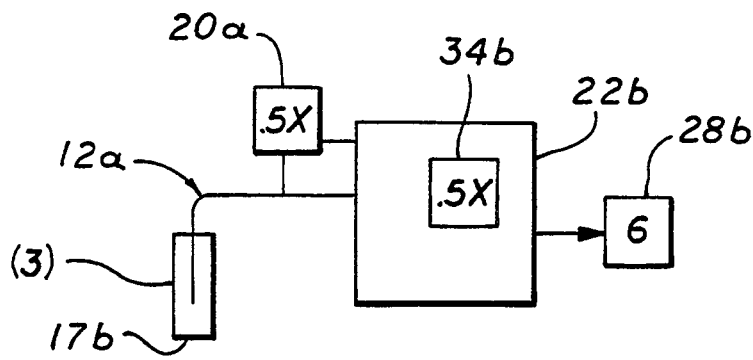
FIGS. 3a–e schematically illustrate a probe's calibration and subsequent transfers according to the method of the present invention.
Figure 3B:
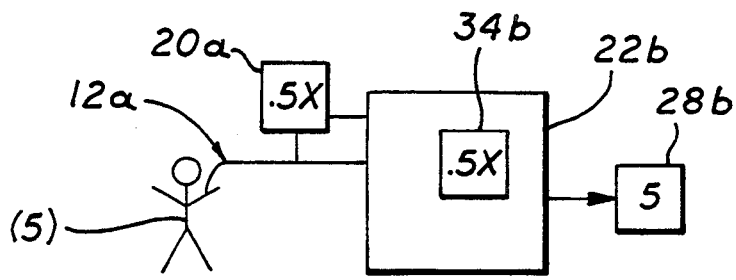
Figure 3C:
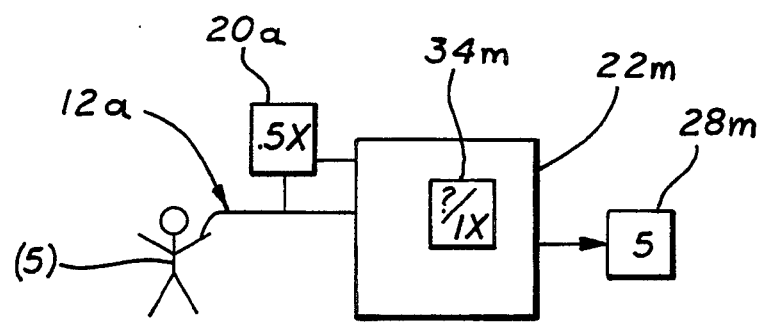
Figure 3D:
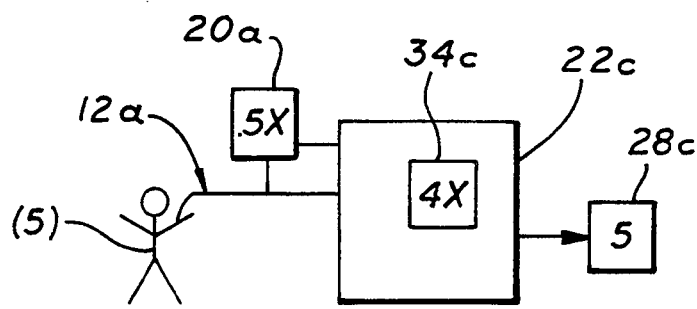
Figure 3E:
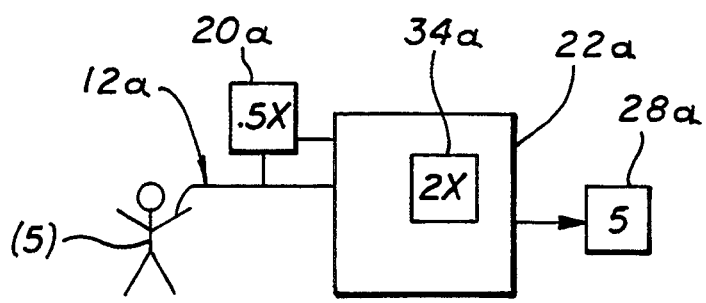

Once all of the non-master instruments in the group (22a, 22b, 22c) have had correction factors entered in their respective memories (34a, 34b, 34c), the measurement system is ready for service. Just prior to use, a probe 12a is interconnected to any one of the instruments of the group, and a probe calibration routine is performed as illustrated in FIG. 3a. The probe is subjected to a calibration standard 17b of precisely known composition, and correction factors are calculated in order to bring output 28b into parity therewith. Such correction factors are stored in the probe's memory 20b. In the example illustrated, the particular combination of instrument 22b and probe 12a with calibration standard 17b yields a value of "6" as modified by the "0.5×" stored in its memory 34b. Because cause the standard's value of "3" requires a further adjustment of "0.5×", such factor is entered in memory 20b. A similar correction factor is entered for every analyte within at least two different calibration standards of known value.

With these correction factors stored in the probe's memory 20a, the probe can then be used with instrument 22b to measure a patient's blood gasses and transferred to any other instrument of the group, including the master instrument 22m to yield precisely the same result. This is schematically illustrated in FIGS. 3b–3e.

Figure 4:
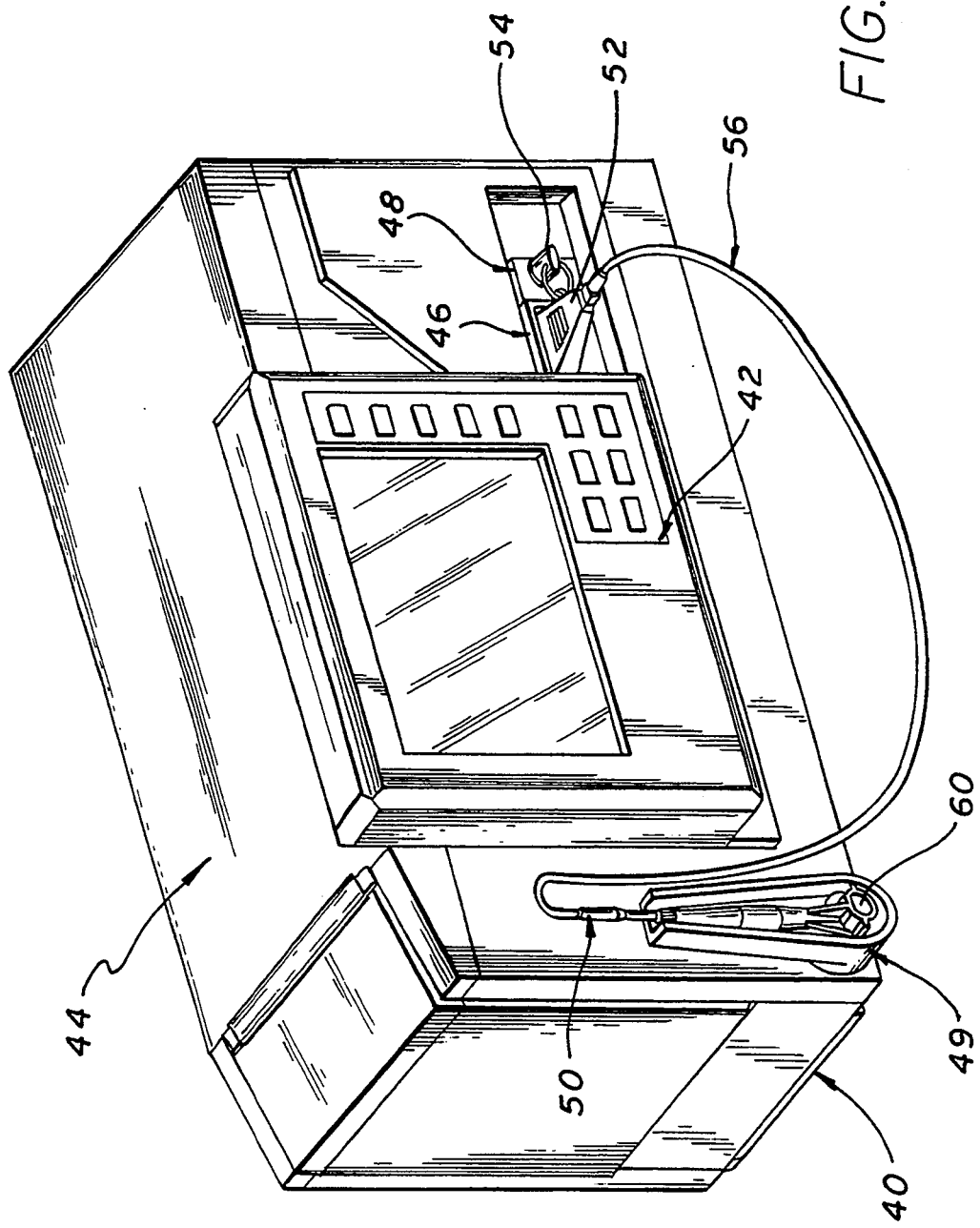
FIG. 4 is a perspective view of one embodiment of the present invention as applied to a blood gas analyzing instrument component and sensor component.

FIG. 4 is a preferred embodiment of the present invention directed to a blood gas analyzer. The instrument component 40 consists of the user display panel 42, the housing 44 for the electronics (not shown), the optical section 46, the receptacle 48 and the calibration gas port 49. The sensor component 50 consists of the optical coupler 52, the memory device 54, the optical fibers 56 and probe (not shown). The analyzer is also equipped with a calibration cuvette 60.

The instrument's optical section 46 is removably attached to the optical coupler 52 of the sensor component 50. Similarly, the instrument's receptacle 48 interconnects to the memory device 54 of the sensor component 50, providing the instrument's electronics access to the sensor's calibration data. In addition, the instrument's port 49 accepts the calibration cuvette 60.

Figure 5:
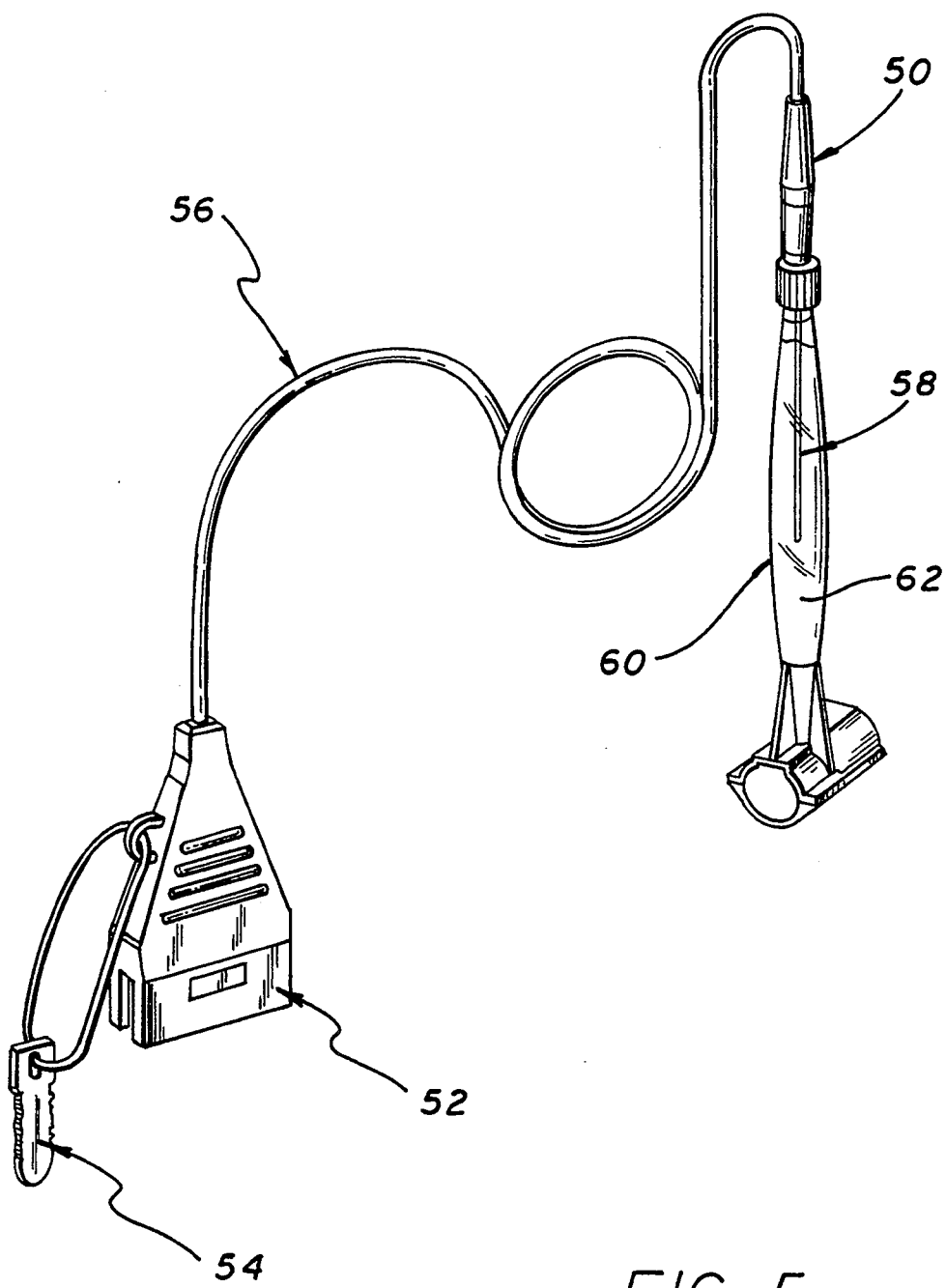
FIG. 5 is an enlarged perspective view of the blood gas sensor component of FIG. 4.

FIG. 5 is an enlarged view of the sensor component 50 portion of the gas analyzer shown in FIG. 4. Memory device 54 is physically and flexibly attached to optic coupler 52. Memory device 54 is a tough, wear-resistant serial portable memory device which houses an electrically erasable programmable read only memory (EEPROM). Alternatively, the memory device may house EPROM, PROM or random access memory (RAM) instead of the EEPROM as the required non-volatile memory. Similarly, the instrument 40 may utilize RAM, PROM, EPROM, or EEPROM as part of the memory device 34 shown in FIG. 1.

For insertion into the instrument receptacle 48 of FIG. 4. memory device 54 is key-shaped. Such a device is available from DATAKEY, Inc., Burnsville, Minn., as Model Nos. DK1000, DK2000 and DK4000 for 1K, 2K, 4K-bit integrated circuit memory. Similarly, a compatible receptacle 48 is available from DATAKEY, Inc. as Model KC4210. In addition, a microcomputer which may interface the memory device and receptacle is available from DATAKEY, Inc. as Model KT4210. For additional information regarding the art of microelectronic memory keys and receptacle systems, see U.S. Pat. Nos. 3,297,579; 4,326,125; 4,379,966 and 4,436,993.

Referring to FIG. 5, sensor component 50 is shown with probe 58, intended for in vivo use in the vasculature of a human patient in a hospital setting. Sensor 50 is adapted to fit into cuvette 60 such that probe 58 is protected by the cuvette 60. The cuvette 60 contains calibration solution 62, or may be filled with a storage solution to preserve the chemistry of the sensing probe 58. Cuvette 60 is adapted to fit into the instrument's gas port 49, as shown in FIG. 4.

While a particular form of the invention has been illustrated and described, it will also be apparent to those skilled in the art that various modifications can be made without departing from the spirit and scope of the invention. Accordingly, it is not intended that the invention be limited except as by the appended claims.

What is claimed is:

1. A measurement apparatus, including a sensor component and an analyzing instrument component, said components being removably connectable, said sensor component being operative to generate a signal in response to certain environmental conditions and said instrument component being operative to generate an output and calibration data interpretive of said signal, comprising:

first memory means secured to said sensor component and interconnectable to said instrument component for storing calibration data relating to said sensor component, wherein said instrument component stores said calibration data into said first memory means;

second memory means located within said instrument component for storing calibration data relating to said instrument component; and processing means for correcting said signal in accordance with said calibration data stored in said first and said second memory means.

2. The measurement apparatus of claim 1, further comprising at least two instrument components, each instrument component interchangeable with the other and having respective memory means for storing calibration data relating to said instrument components, said first memory means having calibration data relating to said sensor component and necessary for said signal to be correctly interpreted by said instrument components.

3. The measurement apparatus of claim 2, wherein said first and second memory means are selected from the group consisting of RAM, PROM, EPROM and EEPROM.

4. The measurement apparatus of claim 1 wherein said sensor component generates an optical signal and wherein said first and said second memory means store calibration data electronically.

5. The measurement apparatus of claim 1 wherein said sensor component comprises at least one probe, insertable into a patient's vasculature, said probe being responsive to the presence of a certain blood parameter within said patient's blood supply and operative to fluoresce with an intensity thereof being a function of the partial pressure of said parameter and wherein said instrument component interprets such fluorescence to generate an output directly in terms of said partial pressure.

6. The measurement apparatus of claim 5, wherein the blood parameter to be measured is selected from the group consisting of $PO_2$, $PCO_2$, and pH.

7. The measurement apparatus of claim 1, wherein said first memory means is removably secured to said sensor component.

8. An invasive optical blood gas analyzer, including a probe insertable into a patient's blood flow, and an analyzing instrument, said probe and instrument being interconnectable, said probe being operative to generate fluorescent radiation, the intensity of said fluorescent radiation being a function of the partial pressure of a certain gas in the patient's blood flow, and said instrument being operative to convert the fluorescent intensity into a measure of partial pressure, said analyzer comprising:

a first, non-volatile, semi-conductor memory device attached to said probe, said first memory device interconnectable to said instrument and operative to store calibration data specific to said probe relating to the conversion of said fluorescent intensity into a measure of partial pressure;

a second, non-volatile, semi-conductor memory device located within said instrument and operative to store calibration data specific to said instrument relating to the conversion of said fluorescent intensity into a measure of partial pressure; and a data processor located within said instrument for correcting the measure of partial pressure in accordance with the calibration data stored in said first and second memory devices.

9. The analyzer of claim 8, wherein said first and second memory devices are selected from the group consisting of RAM, PROM, EPROM and EEPROM.

10. The analyzer of claim 8 wherein the probe is capable of generating fluorescent radiation which is a function of the pH value of the patient's blood.

11. The blood gas analyzer of claim 8, wherein said first memory device is removably attached to said probe.

12. The blood gas analyzer of claim 8, wherein calibration data is stored in said first memory device via an analyzing instrument interconnected thereto.

13. The blood gas analyzer of claim 8, wherein the calibration data stored in said first memory device is specific to the characteristics of said probe.

14. A method for calibrating a group of instruments, said group including at least a first and second instrument, each instrument operative to interpret signals generated by remote sensors interconnectable thereto and responsive to a certain environmental condition, said sensors including memory means for storing calibration data and said instruments including memory means for storing calibration data as well as processing means for interpreting the sensor signals in accordance with calibration data stored in said sensors' and said instruments' memory, said method comprising the steps of:

selecting a first instrument, interconnecting said first instrument to a first sensor, subjecting said first sensor to a first standard of said certain environmental condition to generate a first signal, entering first calibration data into the memory means of said first sensor, generating a first measurement of said first standard;

selecting a second instrument, interconnecting said second instrument to said first sensor and subjecting said first sensor to said first standard to generate a second signal;

entering second calibration data into said second instrument's memory means so as to correct said second signal to conform to said first measurement.

15. The method of claim 14 further comprising the step of subjecting said first sensor to at least one additional standard of certain environmental conditions and interconnecting the first sensor subjected to each additional standard to each of the first and second instruments, so as to obtain additional calibration points to be stored in the memory means of the sensor and instruments.

16. The method of claim 14, further comprising the step of entering an interpretation from said first instrument of said first signal into said first sensor's memory means for correction of an interpretation from said second instrument of said second signal.

17. A method for calibrating an invasive optical blood gas analyzing system, including a group of analyzing instruments, so as to enable a transfer of probes, interconnectable to such analyzing instruments, from instrument to instrument without recalibration, each of said probes including a memory device for storing calibration data and each of said instruments including a memory device for storing calibration data as well as a data processor for modifying said instrument's output in accordance with calibration data stored in said probe's memory and said instrument's memory, comprising the steps of:

selecting a first probe for use as a transfer probe;

interconnecting said transfer probe to a first instrument of said group of instruments and subjecting said probe to at least one calibration standard;

entering said first instrument's output into said transfer probe's memory device;

successively transferring said transfer probe, subjected to said calibration standard, to every other instrument in said group, and entering corrective data into each individual instrument memory device such that each individual instrument's output is modified to conform to said first instrument's output;

selecting a second probe, interconnecting it to any instrument of said group of instruments and subjecting it to a calibration standard of known values;

entering calibration data into said second probe's memory device for modifying the output of the instrument interconnected thereto to conform to said known values, whereby said second probe can then be interconnected to any instrument in the group to yield an accurate output.

18. A method for calibrating a group of apparatuses including at least a first and second instrument component and including at least a first and second sensor component, each instrument component and sensor component being associated with its own memory device capable of storing calibration data values, each sensor component being configured to removably connect to each instrument component, each sensor component configured to be subjected to at least a first known standard of analytes for which each sensor component is capable of detecting, said method including the steps of:

connecting a first sensor component to a first instrument component;

subjecting the first sensor component to a first standard;

calculating calibration values associated with the first sensor component when the first sensor component is connected to the first instrument component and subjected to the first standard;

storing calculated calibration values into the memory device of the first sensor component;

repeating said connecting, subjecting, and calculating steps for the second instrument component connected to the first sensor component subjected to the first standard, wherein new calibration values are calculated and stored into the memory device of the second instrument component.

19. The method of claim 18, further comprising the step of repeating said connecting, subjecting and calculating steps for the first sensor component subjected to the first standard sequentially connected to each instrument component, wherein calibration values are calculated and stored into the memory device of each instrument component.

20. The method of claim 18, further comprising the step of repeating said connecting, subjecting, calculating and storing steps, wherein the first instrument component is connected to the second sensor component and the second sensor component is subjected to the first standard.

21. A measurement system, comprising:
a first instrument component having first memory means for storing first calibration data specific to said first instrument component; and
a sensor component removably connectable to said first instrument component, said sensor component having second memory means for storing second calibration data specific to said sensor component,
wherein said first instrument component generates and stores the first calibration data into the first memory means,
wherein said sensor component generates a signal in response to certain environmental conditions, and
wherein said first instrument component further includes processing means for interpreting the signal generated by said sensor component, the processing means utilizing the calibration data stored in the first and second memory means to interpret the signal.

22. The measurement system of claim 21, further comprising a second instrument component having third memory means for storing third calibration data relating to said second instrument component,
wherein said sensor component is configured as a transfer probe for calibrating said second instrument component,
wherein said first and second instrument components are interchangeably connectable to said sensor component,
wherein said second instrument component generates and stores the third calibration data into the third memory means, and
wherein the second and third memory means have calibration data necessary for the signal generated by said sensor component to be correctly measured by said second instrument component.

23. The measurement system of claim 22, further comprising a second sensor component removably connectable to said first instrument component and said second instrument component, said second sensor component having fourth memory means for storing fourth calibration data relating to said second sensor component,
wherein said second sensor component generates a signal in response to certain environmental conditions,
wherein the first and fourth memory means have calibration data necessary for the signal generated by said second sensor component to be correctly measured by said first instrument component, and
wherein the third and fourth memory means have calibration data necessary for the signal generated by said second sensor component to be correctly measured by said second instrument component.

24. A method for calibrating at least two instruments, each instrument having memory means for storing calibration data, each instrument being interconnectable to at least one sensor responsive to an analyte, each sensor having memory means for storing calibration data, and each instrument having means for processing the calibration data, said method comprising the steps of:
(a) subjecting the first sensor to a first analyte;
(b) interconnecting a first instrument to the first sensor;
(c) generating a first signal from the first sensor;
(d) calculating first calibration data from a first measurement of the first signal;
(e) entering the first calibration data into the memory means of the first sensor;
(f) interconnecting a second instrument to the first sensor;
(g) generating a second signal from the first sensor; and
(h) entering second calibration data in the memory means of the second instrument to calculate a second measurement from the second signal which conforms to the first measurement.

25. The method of claim 24 further comprising the steps of subjecting said first sensor to a second analyte and repeating steps (b) through (h) to enter additional calibration data into the memory means of the first sensor and the second instrument.

26. The method of claim 24 further comprising the steps of selecting a second sensor and repeating steps (a) through (e), wherein the second sensor is used in place of the first sensor.

27. The method of claim 24 further comprising the steps of configuring the first sensor as a transfer probe for calibrating each of a plurality of instruments, and repeating steps (f) through (h) for each of the plurality of instruments.

28. A method of calibrating a group of instruments including, at least, a first and a second instrument, each instrument operative to measure and interpret signals from remote sensors interconnectable thereto, said sensors being responsive to an analyte partial pressure or concentration, said sensors including memory means for storing calibration constants related to said sensor performance and said instruments including memory means for storing calibration constants relating to the correction of said instruments as well as processing means for correcting the measured intensity signals, said method comprising the steps of:
selecting a first instrument, interconnecting said first instrument to a first sensor, subjecting said first sensor to a first analyte standard to generate intensity signals, storing calibration constants in said first instrument's memory means;
selecting a second instrument, interconnecting said second instrument to said first sensor, subjecting said first sensor to said first analyte standard to generate intensity signals; and
entering calibration data into the memory means of said second instrument to correct said intensity signals of said second instrument to conform to the intensity signals of said first instrument.

29. A method of calibrating a group of instruments including, at least, a first and a second instrument, each instrument operative to measure and interpret signals from remote sensors interconnectable thereto, said sensors being responsive to an analyte partial pressure or concentration, said sensors including memory means for storing calibration constants related to said sensor performance and said instruments including memory means for storing calibration constants relating to the correction of said instruments as well as processing means for correcting a measured signals, said method comprising the steps of:

selecting a first instrument, interconnecting said first instrument to a first sensor, subjecting said first sensor to one or more analyte standards to generate intensity signals related to known analyte levels, storing calibration constants into said first instrument's memory means;

selecting a second instrument, interconnecting said second instrument to said first sensor and subjecting said first sensor to one or more analyte standards to generate intensity signals related to known standards; and entering calibration data into the memory means of said second instrument to append said calibration data to the memory means of any sensor subsequently calibrated by the second instrument.

30. A method for calibrating at least two instruments each having memory means for storing calibration data, each instrument interconnectable to at least one sensor responsive to an analyte, each sensor having memory means for storing calibration data, and each instrument having means for processing the calibration data, said method comprising the steps of:

(a) interconnecting a first sensor and a first instrument;
(b) subjecting the first sensor to a first analyte;
(c) generating a first signal from the first sensor;
(d) storing a representation of the first signal into the memory means of the first instrument;
(e) interconnecting the first sensor and a second instrument;
(f) generating a second signal from the first sensor;
(g) storing a representation of the second signal into the memory device of the second instrument; and
(h) utilizing the first signal and second signal representations in the memories of the first and second instruments to maintain the accuracy of calibration of all subsequent sensors calibrated on the first instrument and subsequently moved to the second instrument.

* * * * *